United States Patent
Duchon et al.

(10) Patent No.: US 7,101,352 B2
(45) Date of Patent: Sep. 5, 2006

(54) PRESSURE SLEEVE ASSEMBLY

(75) Inventors: Douglas Duchon, Chanhassen, MN (US); James Ryan Mujwid, Burnsville, MN (US)

(73) Assignee: Acist Medical Systems, Inc., Eden Prairie, MN (US)

(*) Notice: Subject to any disclaimer, the term of this patent is extended or adjusted under 35 U.S.C. 154(b) by 552 days.

(21) Appl. No.: 10/636,003

(22) Filed: Aug. 7, 2003

(65) Prior Publication Data

US 2004/0030288 A1 Feb. 12, 2004

Related U.S. Application Data

(63) Continuation of application No. 09/577,906, filed on May 24, 2000, now Pat. No. 6,673,048.

(51) Int. Cl.
*A61M 37/00* (2006.01)
*A61M 5/00* (2006.01)

(52) U.S. Cl. .................. 604/154; 604/232

(58) Field of Classification Search ............ 604/131, 604/151, 154, 155, 181, 232, 233, 234, 235
See application file for complete search history.

(56) References Cited

U.S. PATENT DOCUMENTS

| | | | |
|---|---|---|---|
| 1,157,552 A * | 10/1915 | Kispert | 604/233 |
| 2,627,270 A * | 2/1953 | Glass | 604/155 |
| 3,731,679 A | 5/1973 | Wilhelmson et al. | |
| 3,739,943 A | 6/1973 | Wilhelmson et al. | |
| 4,512,764 A | 4/1985 | Wunsch | |
| 4,535,820 A | 8/1985 | Raines | |
| 4,559,036 A | 12/1985 | Wunsch | |
| 4,677,980 A * | 7/1987 | Reilly et al. | 600/432 |
| 4,854,324 A | 8/1989 | Hirschman et al. | |
| 4,966,199 A | 10/1990 | Ruschke | |
| 4,966,579 A | 10/1990 | Polaschegg | |
| 5,226,886 A | 7/1993 | Skakoon et al. | |
| 5,249,579 A | 10/1993 | Hobbs et al. | |
| 5,254,101 A | 10/1993 | Trombley, III | 604/207 |
| 5,267,964 A | 12/1993 | Karg | |
| 5,346,470 A | 9/1994 | Hobbs et al. | |
| 5,494,036 A | 2/1996 | Uber, III et al. | |
| 5,515,851 A | 5/1996 | Goldstein | |
| 5,569,181 A | 10/1996 | Heilman et al. | |
| 5,573,515 A * | 11/1996 | Wilson et al. | 604/236 |
| 5,739,508 A | 4/1998 | Uber, III | |
| 5,779,675 A * | 7/1998 | Reilly et al. | 604/131 |
| 5,795,333 A | 8/1998 | Reilly et al. | |

(Continued)

FOREIGN PATENT DOCUMENTS

WO    WO 99/21600    * 5/1999

*Primary Examiner*—Sharon Kennedy
(74) *Attorney, Agent, or Firm*—Kramer, Levin, Naftalis & Frankel LLP

(57) ABSTRACT

A pressure sleeve assembly and a method of its use in a fluid injection system are disclosed. The pressure sleeve assembly includes a longitudinal base member, an endplate associated with the longitudinal base member, a fixed or freely removable door, a cylinder and a pivotal arm coupling the cylinder to the longitudinal base member. The pressure sleeve assembly includes properties that increase the ease of use and maintenance of the assembly so as to reduce the effort required by the user and increase the biosafety aspect of the assembly. In addition, the pressure sleeve assembly includes properties that reduce the amount of effort required by the physician prior to and during use of the system as well as properties that increase its range of applications.

15 Claims, 6 Drawing Sheets

U.S. PATENT DOCUMENTS

| | | | |
|---|---|---|---|
| 5,800,397 A * | 9/1998 | Wilson et al. | 604/151 |
| 5,806,519 A | 9/1998 | Evans, III et al. | |
| 5,807,340 A * | 9/1998 | Pokras | 604/183 |
| 5,808,203 A | 9/1998 | Nolan, Jr. et al. | |
| 5,840,026 A | 11/1998 | Uber, III et al. | |
| 5,843,037 A | 12/1998 | Uber, III | |
| 5,873,861 A | 2/1999 | Hitchins et al. | |
| 5,885,216 A | 3/1999 | Evans, III et al. | |
| 5,899,855 A * | 5/1999 | Brown | 600/301 |
| 5,916,165 A * | 6/1999 | Duchon et al. | 600/431 |
| 5,920,054 A | 7/1999 | Uber, III | |
| 5,947,935 A | 9/1999 | Rhinehart et al. | |
| 6,007,515 A * | 12/1999 | Epstein et al. | 604/82 |
| RE36,648 E | 4/2000 | Uber, III et al. | |
| 6,086,569 A * | 7/2000 | Schweizer | 604/227 |
| 6,096,011 A | 8/2000 | Trombley, III et al. | |
| 6,099,502 A * | 8/2000 | Duchon et al. | 604/131 |
| 6,149,627 A | 11/2000 | Uber, III | |
| 6,197,000 B1 | 3/2001 | Reilly et al. | |
| 6,270,481 B1 * | 8/2001 | Mason et al. | 604/181 |
| 6,306,117 B1 | 10/2001 | Uber, III | |
| 6,317,623 B1 | 11/2001 | Griffiths et al. | 600/431 |
| 6,339,718 B1 | 1/2002 | Zatezalo et al. | |
| 6,344,030 B1 * | 2/2002 | Duchon et al. | 604/131 |
| RE37,602 E | 3/2002 | Uber, III et al. | |
| 6,385,483 B1 | 5/2002 | Uber, III et al. | |
| 6,387,077 B1 * | 5/2002 | Klibanov et al. | 604/181 |
| 6,397,098 B1 | 5/2002 | Uber, III et al. | 600/431 |
| 6,402,717 B1 | 6/2002 | Reilly et al. | 604/67 |
| 6,440,107 B1 | 8/2002 | Trombley, III et al. | |
| 6,442,418 B1 | 8/2002 | Evans, III et al. | |
| 6,471,674 B1 | 10/2002 | Emig et al. | |
| 6,475,192 B1 | 11/2002 | Reilly et al. | 604/189 |
| 6,520,930 B1 | 2/2003 | Critchlow et al. | |
| 6,643,537 B1 | 11/2003 | Zatezalo et al. | |
| 6,652,489 B1 | 11/2003 | Trocki et al. | 604/154 |
| 6,673,033 B1 | 1/2004 | Sciulli et al. | 604/67 |
| 6,699,219 B1 | 3/2004 | Emig et al. | 604/131 |
| 6,731,971 B1 | 5/2004 | Evans, III et al. | |
| 6,733,477 B1 | 5/2004 | Cowan et al. | 604/181 |
| 6,733,478 B1 | 5/2004 | Reilly et al. | 604/189 |
| 6,743,202 B1 | 6/2004 | Hirschman et al. | 604/131 |
| 6,889,074 B1 | 5/2005 | Uber, III et al. | 600/431 |
| 6,901,283 B1 | 5/2005 | Evans, III et al. | 600/431 |
| 6,939,302 B1 | 9/2005 | Griffiths et al. | 600/458 |

* cited by examiner

PRESSURE SLEEVE ASSEMBLY

RELATED APPLICATIONS

This application is a continuation of U.S. patent application Ser. No. 09/577,906, filed May 24, 2000, now U.S. Pat. No. 6,673,048, issued Jan. 6, 2004.

FIELD OF THE INVENTION

The present invention relates generally to fluid injection systems. The present invention particularly relates to a pressure sleeve for housing a syringe usable for injection of fluids in medical procedures such as angiography, magnetic resonance imaging (MRI), computer tomography (CT) and radiology. In addition, the invention relates to a pressure sleeve assembly that allows for front and/or rear loading and removal of a syringe.

BACKGROUND OF THE INVENTION

Fluid injection systems are used in numerous medical procedures that require injection of fluid into a patient. One non-limiting example of such a procedure is the treatment of coronary artery disease where an artery feeding into the heart has become obstructed or narrowed. In such conditions, an angioplasty, or stent placement, is often a prescribed treatment and in preparing for such procedures, an angiogram is performed.

In such procedures, a large volume of a radio-opaque "dye" or contrast media is injected into the vasculature of the patient to the site of obstruction. X-ray videos are then taken of the coronary arteries using the contrast media, thus providing an image of the location and severity of the blockage in the diseased vessel.

Due to the pressure and large volume of fluid being injected into a patient during cardiological procedure and many other types of procedures (e.g. MRI, CT, etc.), specialized injection systems have been developed which enclose and retain the injecting syringes during use. These systems typically use a disposable syringe since non-disposable syringes can oftentimes be impractical and prohibitive from a cost and process standpoint. Such systems restrict and prevent bursting or leakages of the pressurized fluid during use of the injecting syringe. Due to the safety and reliability requirements of systems containing such pressurized fluids, various pressure sleeve systems have been developed for medical use. Examples of these systems can be found in U.S. Pat. No. 5,899,885 and U.S. Pat. No. 5,779,675.

In each of the above-referenced patents, there is disclosed a fluid injection system that utilizes a specialized pressure sleeve designed to accommodate the biosafety requirements for each injection system. These pressure sleeve designs are also intended to simplify the operation of the injector by enabling the user to introduce the syringe into the injection system from the front of the system. Such designs are typically referred to as "front-loading" injection systems.

Although the front-loading systems disclosed in the above-referenced patents (and other similar devices not specifically described) offer improvements over the earlier pressure sleeve designs, such systems are not always optimal. For example, one disadvantage of a front-loading pressure sleeve design as shown is that a user can accidentally attempt to remove the syringe from the system when the syringe plunger is still engaged (at the rear end of the plunger) to the actuator ram of the injection system. If the syringe is successfully removed with the plunger still attached to the actuator, any remaining injection fluid will flood the pressure sleeve assembly and likely seep onto the actuator and eventually into the injector housing. Although not creating a biohazard, this undesirable result may somewhat reduce long term performance and thus, requires disassembly of the sleeve in order to thoroughly clean the system.

Another example of a disadvantage of the front-loading system such as discussed above is the difficulty in removing the syringe and/or pressure sleeve from the system if there has been any leakage or inadvertent spilling of injection media into the pressure sleeve. This difficulty results from the injection media solidifying or accumulating on the pressure sleeve surfaces and thereby inhibiting smooth movement of the syringe into or out of the pressure sleeve, as well as movement of the pressure sleeve out of the injector. Oftentimes, the only way to remove the syringe and/or pressure sleeve under such conditions is to pry the device out by hand or with some sort of makeshift tool.

In view of the above, it is apparent that although improvements in pressure vessel sleeves have been made, there is a continuing need to provide better pressure sleeve systems that are reliable and less likely to result in fluid contamination of the pressure sleeve assembly. There is also a need to provide an injection device having a pressure sleeve system that is simpler to use and easier to maintain. Such improved fluid injection systems include properties that reduce the amount of effort required prior to and during use of the system as well as properties that increase the device's range of applications.

OBJECTS AND SUMMARY OF THE INVENTION

In view of the foregoing, it is an object of the present invention to provide a pressure sleeve assembly that addresses the limitations and disadvantages associated with prior devices, yet meets the needs of the users.

A further object of the invention is to provide a pressure sleeve assembly that is efficient, requires minimal effort by the user, is easy to assemble, disassemble and maintain.

Still another object of the invention is to provide a pressure sleeve assembly that is freely accessible. Such an assembly allows for changing syringe configurations for use in different applications.

A further object of the invention is to provide a pressure sleeve assembly having a pivotable pressure sleeve. This configuration allows for a fully exposed sleeve, which increases its accessibility and ease of cleaning. A pivotable pressure sleeve can have a permanently mounted door, thereby creating a "chamber" area for the syringe. Alternatively, the pressure sleeve can be stationary and have a removable door.

A further object of the invention is to provide an axial force management system such that a forward plate of the injector is rigidly mounted to the support and can withstand the primarily axial forces being exerted against a syringe mounted in a pressure sleeve.

A further object of the invention is to provide a pressure sleeve assembly configured so as to have a pressure transducer or sensor coupled to or located within or on the front plate thereby providing a direct and more accurate measurement of fluid pressure within the syringe.

An additional object of the invention is to provide an injection system for delivery of contrast media or other fluids. The system can include a power supply, an injector head, a console and a pressure sleeve assembly, where the pressure sleeve assembly can have a longitudinal base member having a receptacle area, a cylinder having a first opening and a second opening, a pivotal arm movable between a first position and a second position, coupling the cylinder to the longitudinal base member, where the cylinder is exposed when in the open position and resides within the receptacle area of the longitudinal base member when in the closed position, and a door positioned at the first opening of the cylinder in the closed position, where the door is fixed to the longitudinal base member.

These and other objects not specifically enumerated herein are believed to be addressed by the present invention, which contemplates a pressure sleeve assembly and its use with a fluid injection system for delivery of fluids during numerous types of medical procedures.

DETAILED DESCRIPTION OF THE INVENTION

Figure 1:
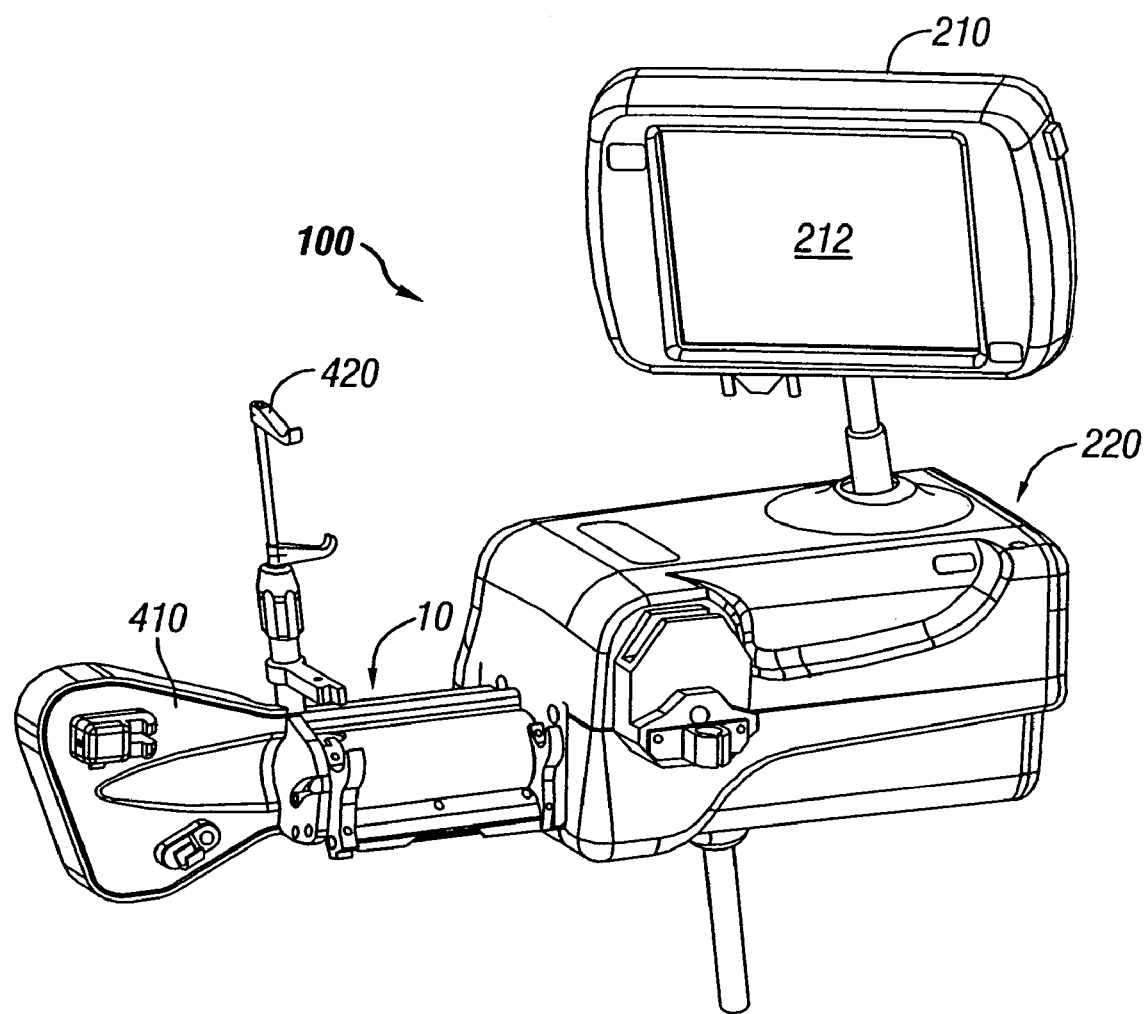
FIG. 1 is a perspective view of one preferred embodiment of an injection device in accordance with the present invention.

FIGS. 1–9 show various embodiments of a pressure sleeve assembly usable in a fluid injector system such as described in co-pending U.S. application Ser. No. 08/488,443 filed Jan. 20, 2000, U.S. application Ser. No. 08/966,088 filed Nov. 7, 1997, U.S. application Ser. No. 08/957,228 filed Oct. 24, 1997 and U.S. application Ser. No. 08/957,801 filed Oct. 24, 1997, as well as U.S. Pat. Nos. 5,800,397, 5,988,587 and 5,573,515, the disclosures of which are hereby incorporated by reference in their entirety. Referring particularly to FIG. 1, an injector system includes an injector head 220 upon which a display screen 210 is mounted. A power supply (not shown) is connected to the injector head 220. At one end of the injector head is located the structure that holds a syringe during an injection. This structure includes a pressure sleeve assembly.

Generally, a pressure sleeve assembly can be used for delivery of fluid, such as contrast media, to a patient during a medical procedure. Typically a pressure sleeve assembly is used to house and provide support for a syringe through which fluid is injected into a catheter line feeding into a patient. When a fluid-filled syringe is contained within the pressure sleeve assembly, the forward motion of an actuator (coupled to the rear end of a plunger or wiper of the syringe) drives the fluid forward from the syringe into a catheter attached to the syringe. Due to the pressure forces generated within a syringe during fluid delivery, a pressure sleeve assembly is desirable for containment and support of the syringe. Any of the pressure sleeve assemblies described herein may be used in a fluid delivery system for housing a syringe component.

FIGS. 2–7 show a first embodiment of a pressure sleeve assembly 10, which includes a longitudinal base member 20 having a receptacle area 30, a cylinder 40 for housing a syringe, a pivotal arm structure 50, a faceplate 62 that is connected with the longitudinal base member 20, and a stationary forward plate 60. The cylinder 40 is mounted on the pivotal, or "hinged," arm structure 50, which, in turn, is movable between a closed position (FIGS. 5–7) where the cylinder 40 is disposed in the receptacle area 30 and an open position (FIGS. 1–3), where the cylinder 40 is disposed away from the receptacle area 30.

The cylinder 40 includes a first opening 44 which is covered by the forward plate 60 when in the closed position, and a second opening 46 which is covered by the endplate 62 when in the closed position. The endplate 62 is attached to the end of the longitudinal base member 20 generally along two of the endplate's four sides.

Figure 2:
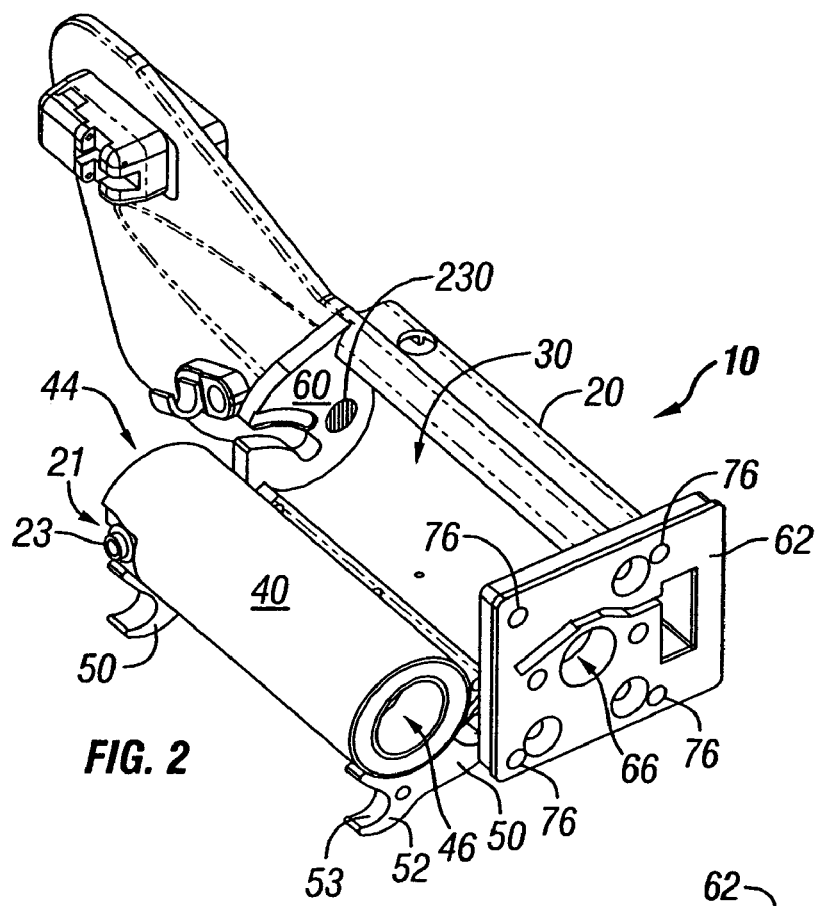
FIG. 2 is a first perspective view of a preferred embodiment of a pressure sleeve assembly in an open position in accordance with the present invention.
Figure 3:
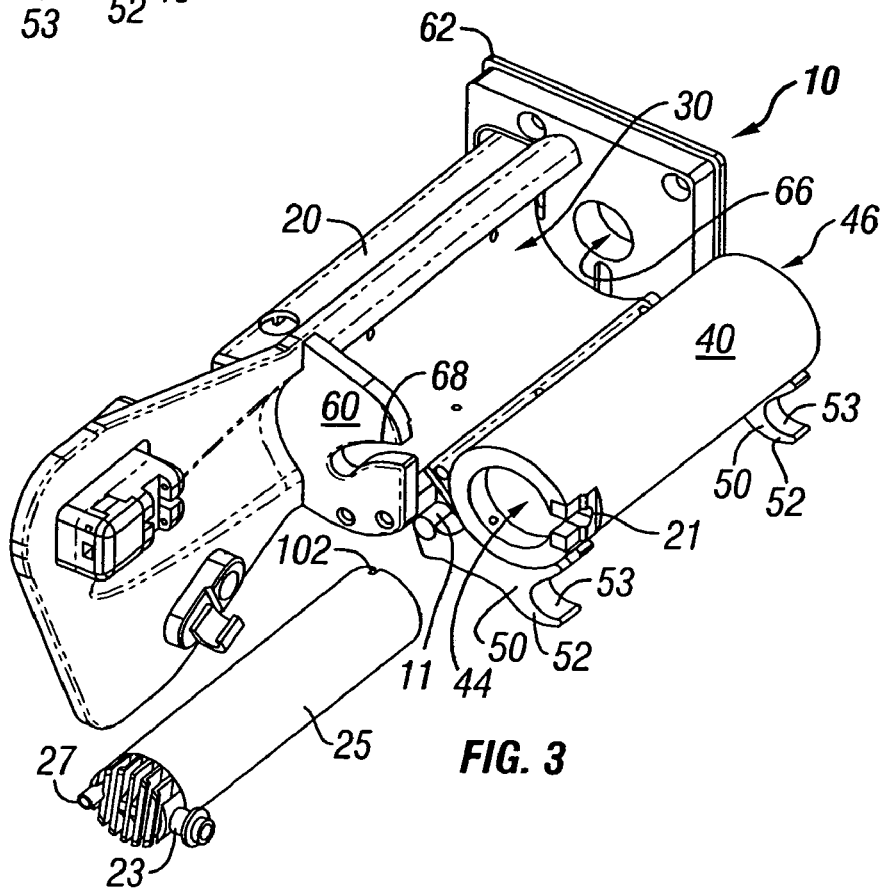
FIG. 3 is a second perspective view of a preferred embodiment of a pressure sleeve assembly in an open position in accordance with the present invention.

As described above (and with reference to the referenced patents and application), a pressure sleeve assembly 10 typically receives a syringe 25 that contains or holds the fluid that is or will be injected into a patient. With reference to FIGS. 2–3, the syringe 25 is placed within the cylinder 40 of the assembly 10 and the fluid is moved by an actuator (not shown) that pushes a wiper or syringe plunger of the syringes forward to dispense fluid or backward to fill the syringe 25. Therefore, the endplate 62 of the pressure sleeve assembly 10 has an opening 66 through which the actuator extends and contacts the rear surface of a wiper or plunger of the syringe. The fluid within the syringe is pushed forward by movement of the actuator against the wiper of the syringe. Therefore, the opening 66 of the endplate 62 will be axially aligned with the second opening 46 of the cylinder 40 when the pivotal, or "hinged," arm structure 50 is in the closed position so as to allow free extension and retraction of the actuator into the cylinder 40. The endplate 62 can also include structures or holes 76, which allow for its connection or attachment to other elements or structural supports in the fluid injection system.

Figure 5:
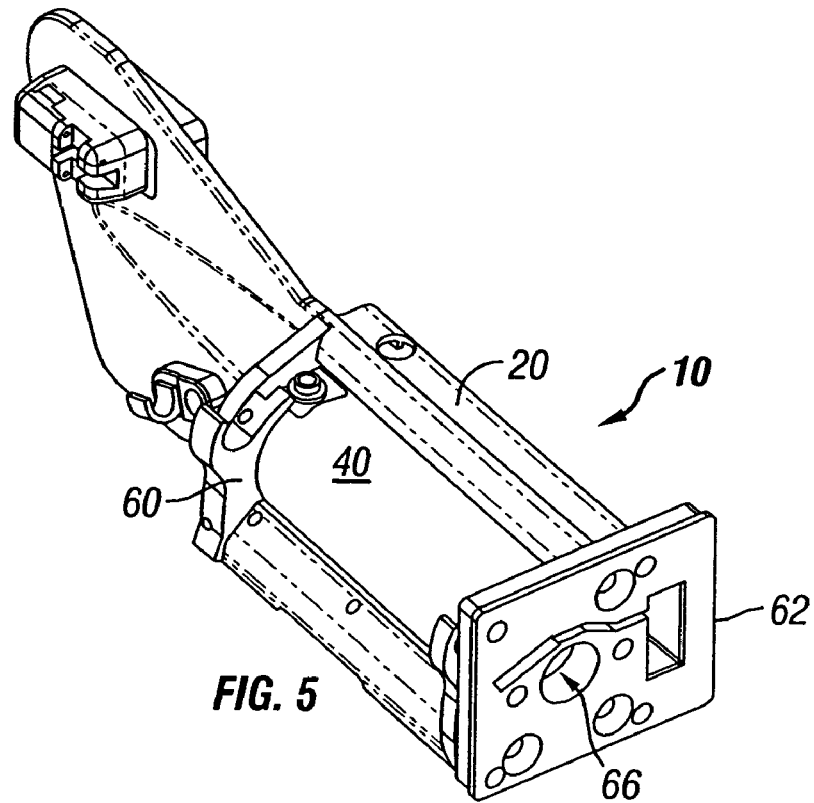
FIG. 5 is a first perspective view of a preferred embodiment of a pressure sleeve assembly in a closed position in accordance with the present invention.
Figure 6:
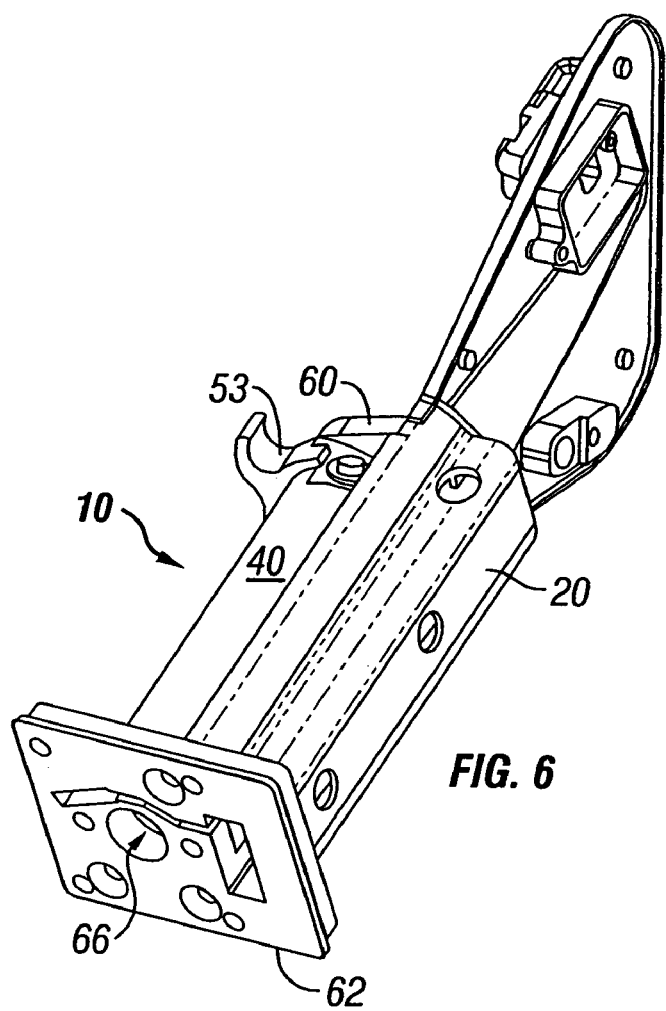
FIG. 6 is a second perspective view of a preferred embodiment of a pressure sleeve assembly in a closed position in accordance with the present invention.
Figure 7:
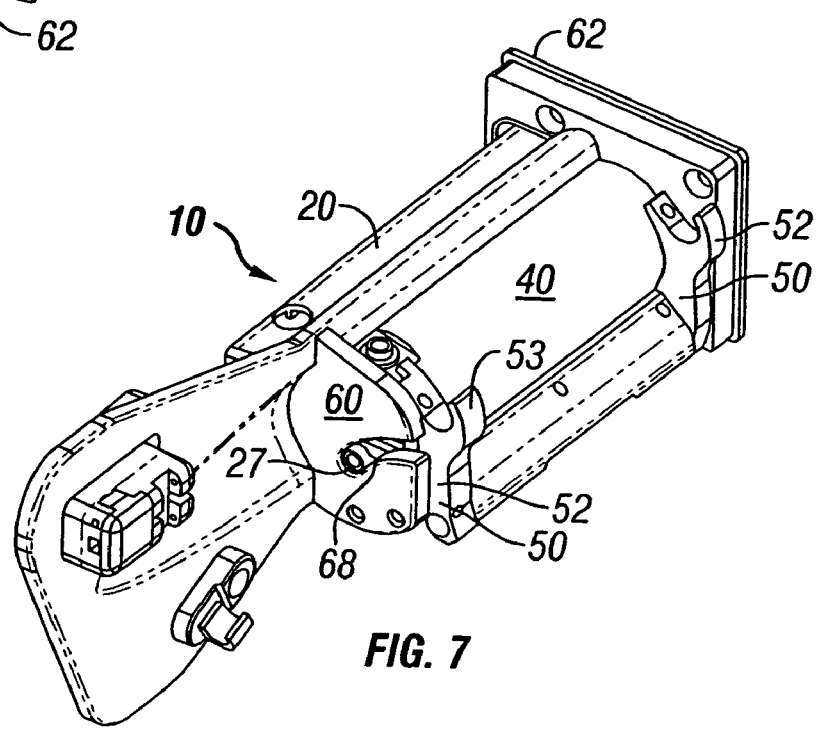
FIG. 7 is a third perspective view of a preferred embodiment of a pressure sleeve assembly in a closed position in accordance with the present invention.

Perspective views of the pressure sleeve assembly 10 with the arm structure 50 in a closed position (during fluid injection) are shown in FIGS. 5–7.

Referring to FIG. 3, when the arm structure 50 is in the open position, a syringe 25 is generally loaded into the first opening 44, but, with certain designs, the syringe 25 can be loaded through the second opening 46. In this embodiment of the present invention (also referred to herein as the "rotatable cylinder" embodiment), the cylinder 40 of the pressure sleeve assembly 10 is coupled to the longitudinal base member 20 by an arm structure 50 that includes a pair of supports 52. One support 52 is attached at a location on the longitudinal base member 20 near the first opening 44 of the cylinder 40. The second support 52 is attached to a location on the longitudinal base member 20 near the second opening 46 of the cylinder. The support 52 located near the first opening 44 includes a grasping surface 53 that serves as a surface for the user to pull and push the cylinder 40 into and out of the receptacle area 30, respectively.

Use of a pivotal, or "hinged," arm structure 50 allows for exposure of the cylinder 40 by a rotational/pivotal movement and, thus, allows axial insertion of the syringe into the pressure sleeve and "radial" loading of a syringe into the closed portion of the receptacle area 30. Any type of fastener, hinge or attachment mechanism that allows for radial or rotational movement of the pivotal arm structure 50 can be used to connect the pivotal arm 50 to the longitudinal base member 20. In the embodiment shown, an elongated hinge structure 11 is utilized. The longitudinal base member 20 provides the primary structural support platform for the cylinder 40, the endplate 62 and forward plate 60. The endplate 62, forward plate 60 and cylinder 40, together create a chamber within which a syringe can be retained during fluid injection. After the syringe is inserted into the cylinder 40, when the arm structure 50 is in the open position, the cylinder 40 can be pushed or rotated into the receptacle area 30 place into the closed position, thus placing the syringe into a position for performing a fluid injection.

The rotatable pressure sleeve assembly 10 having the pivotal arm structure 50 discussed above allows for a cylinder 40 that can remain attached to the pressure sleeve assembly 10, but can still be fully exposed. This advantage aids in the removal and cleaning of the syringe and the cylinder 40, since the motion and effort required for pulling or "extracting" out a syringe and/or cylinder 40 is simpler than that requiring sliding or "prying" out a non-rotating cylinder. Therefore, a rotatable pressure sleeve assembly 10 having fully exposable cylinder 40 provides easy access to component parts for cleaning or other manipulation.

An additional feature of a rotatable pressure sleeve assembly 10 that is advantageous is that in order to remove the syringe contained within the cylinder 40, the user must pivot the arm structure 50 (and thus the cylinder 40) away from the longitudinal base member 20. Before this pivotal movement can take place, the user must first ensure that the wiper or plunger of the syringe is disengaged from the actuator. As a result, with the rotatable pressure sleeve assembly 10, the user cannot accidentally remove the syringe with the wiper/plunger still connected to the actuator. This result reduces the chances of flooding the cylinder with fluid, thereby further increasing the reliability aspect of this invention.

The rotational movement of the rotatable pressure sleeve 10 is similar to that of the bullet chamber in a revolver firearm. That is, the cylinder 40 or "barrel" of the assembly can be unlocked, and rotated (via the arm structure 50) out of the closed position to expose the "full chamber" of the cylinder 40 (FIG. 2). Once the "barrel" is exposed or open (FIG. 3), the syringe is slid into the first opening 44 of the cylinder 40 (FIG. 4) and the cylinder 40 containing the syringe is rotated back into its initial, closed position (FIGS. 5–7). To lock the cylinder 40 and arm structure 50 in the closed position, the cylinder 40 can preferably include thermoplastic polymers such as polycarbonate, amorphous nylon, PET, acrylic or any other suitable clear plastic.

Figure 10:
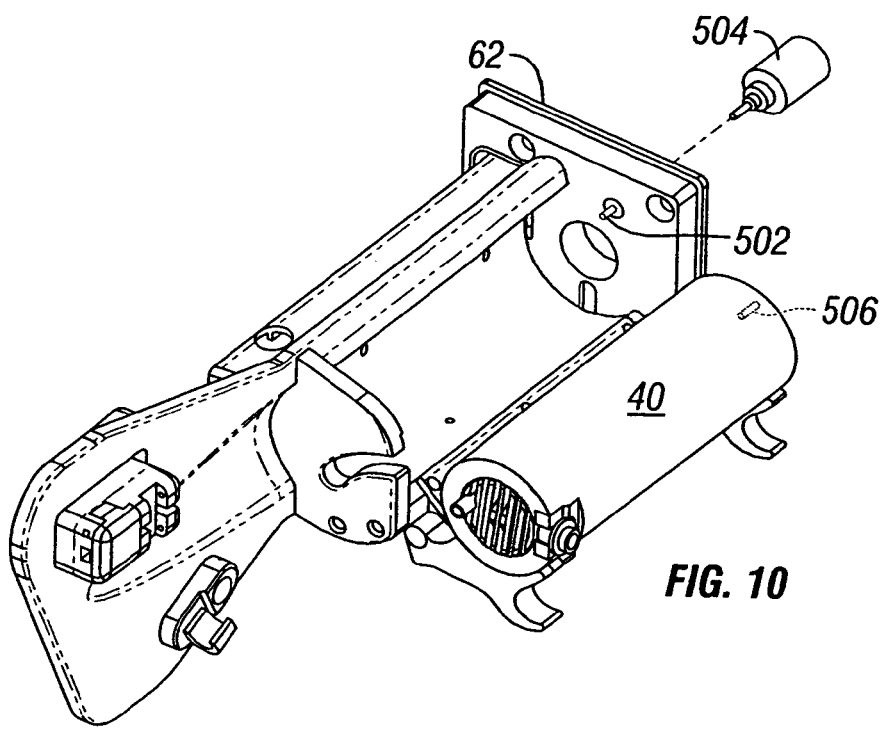
FIG. 10 is a perspective view of a preferred embodiment of a pressure sleeve assembly in accordance with the present invention which includes a pressure sleeve locking device; and, FIG. 11 is a perspective view of a preferred embodiment of a pressure sleeve assembly in accordance with the present invention, which includes a device for sensing closure of the assembly.
Figure 11:
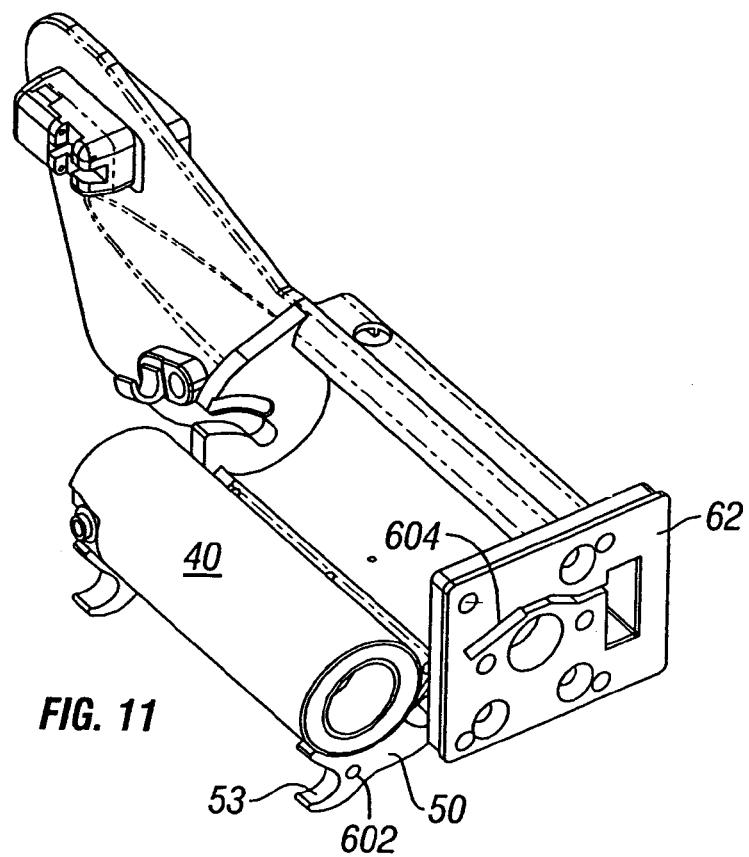

Referring to FIGS. 10 and 11, there is disclosed a number of ways of sensing and locking the pressure cylinder 40 into place. For example, referring to FIG. 10, an axially movable pin 502 may be disposed in the backplate 62 for engagement with a pin receptacle 506 in the cylinder 40. Furthermore, the pin could be actuated by a solenoid or other control mechanism 504. In use, once it is determined that the pressure cylinder 40 is in the closed position, the solenoid 504 could be actuated such that the pin extends forward and is received in the receptacle 506 of the cylinder 40. The cylinder 40 then remains locked in the closed position until reverse actuation of the pin 502 occurs. Control of the pin actuation can be done automatically through the injection machine control system or manually by the user.

Referring to FIG. 11, a sensor mechanism is disclosed including a permanent magnet 602 mounted in near the grasping surface 53 of the arm structure 50 and a hall effect sensor 604 mounted in the backplate 62. When the cylinder 40 has been rotated into the closed position, the permanent magnet 602 is located near enough to the hall effect sensor 604 to trigger a signal that indicates to the user that the cylinder has been moved into the closed position. The hall effect sensor 604 is typically in communication with the injector control system such that triggering of the sensor will serve as a safety to dictate when performance of an injection may be safely performed.

Figure 4:
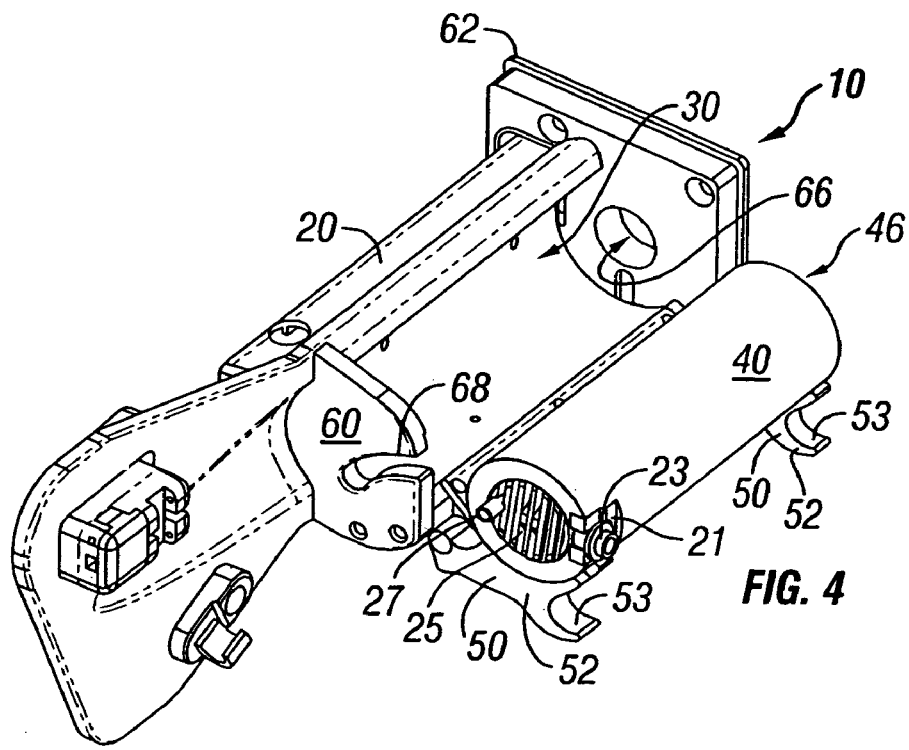
FIG. 4 is a third perspective view of a preferred embodiment of a pressure sleeve assembly in an open position in accordance with the present invention.

Referring to FIGS. 2–4, another aspect of the rotatable pressure sleeve 10 in accordance with the present invention is a slot 21 located in the cylinder 40 for receiving the stem 23 of the fluid fill port of the syringe 25. The slot 21 is located at a location on the cylinder 40 so that the stem 23 is protruding substantially vertically upwardly from the cylinder 40 when the cylinder 40 has been rotated into the closed position. The slot 21 also serves a "keying" function insofar as a cylinder 40 loaded with a syringe cannot be rotated into the closed position unless the stem 23 of the syringe 25 has been "keyed" into place into the slot 21. If the stem 23 is not "keyed" into place into the slot 21, a portion of the syringe 25 will remain protruding from the cylinder 40 and thus prevent rotation of the cylinder 40 into the closed position.

In another aspect of the invention, the front plate 60 includes a curved slot 68, which receives, and guides a fluid exit port 27 of the syringe 25 as the cylinder 40 is rotated into the closed position. As with the slot 21 for receiving the stem 23 of the syringe 25, the curved slot 68 also serves to ensure that the syringe 25 has been properly inserted/loaded into the cylinder 40. If not properly "keyed" into the curved slot 68 the cylinder 40 cannot be properly rotated into the closed position. Furthermore, as with the slot 21, the curved slot 68 ensures that the syringe 25 is properly inserted for engagement with the actuator once the cylinder 40 has been rotated into the closed position.

In addition to the two "keying" features discussed above, the present invention contemplates an indexing feature for further controlling the placement of the syringe 25 into the pressure sleeve 10. The indexing feature includes an indentation or slot 102 located at one end of the syringe 25. This slot mates with a corresponding protrusion (not shown) located on the internal surface of the cylinder 40. In order for the syringe to be inserted properly into the cylinder 40, the slot 102 must be aligned correctly with the mating protrusion so that the two structures mate and thus allow full insertion of the syringe 25 into the cylinder 40. In this connection, the reader is referred to similar types of indexing features as set forth in co-pending U.S. application Ser. No. 09/542422, entitled Fluid Management and Component Detection System, filed Apr. 21, 2000, and the disclosure of which is hereby incorporated by reference in its entirety.

One notable advantage of the rotatable pressure sleeve 10 of the present invention is that a sensing device 230 (FIG. 2) may be placed in or on the stationary forward plate 60 to engage with the front surface of the syringe 25. Specifically, the forward plate 60 can be designed to include a load cell 230 or other sensor which, through the controller of the device, will allow for a direct measurement of the force or pressure (force/unit area) being exerted by the actuator on the syringe. In this connection, the load cell 230 can be used to detect the syringe "dry" (no fluid present) friction at several speeds which allows for the computation and characterization of the inherent frictional losses within the syringe at various positions and velocities of the wiper. Such information can be stored and used for a more accurate determination of the actual pressure being exerted during injection of fluid. Another potential use of the sensor 230 is as a detector of the presence of the syringe 25 in the receptacle area 30. For example, if the pressure sleeve 40 has been rotated into the closed position but there has been no syringe 25 placed into the pressure sleeve 40, then there is no structure from which the actuator could exert pressure on the sensor 230. The absence of such pressure as sensed by the sensor 230 could be used to indicate that there is no syringe present in the sleeve 40. Examples of load cells usable in this manner are products made by Entran.

Figure 8:
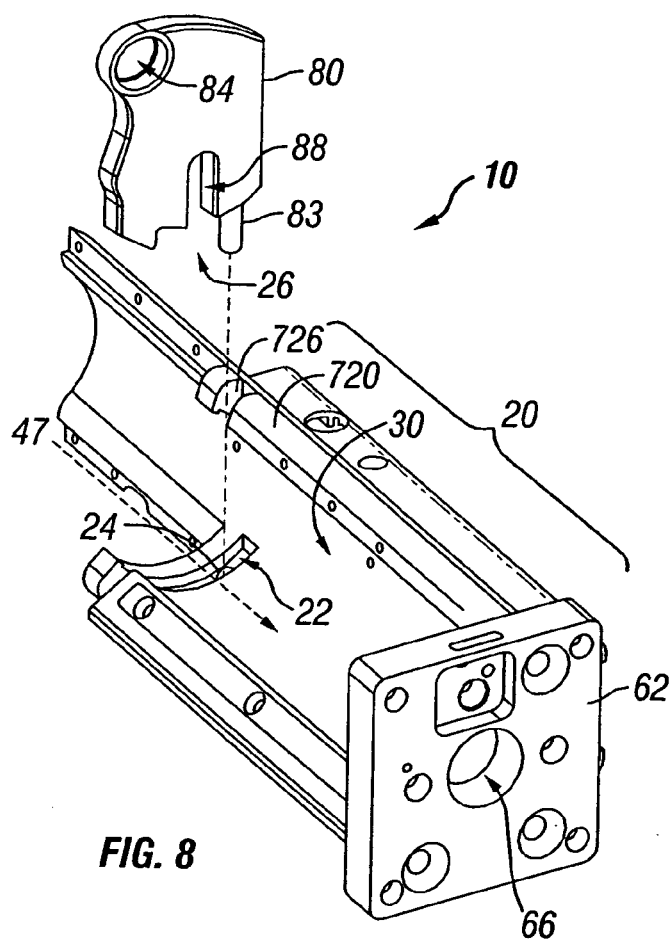
FIG. 8 a perspective view of a preferred embodiment of a pressure sleeve assembly in accordance with the present invention having a removable door.
Figure 9:
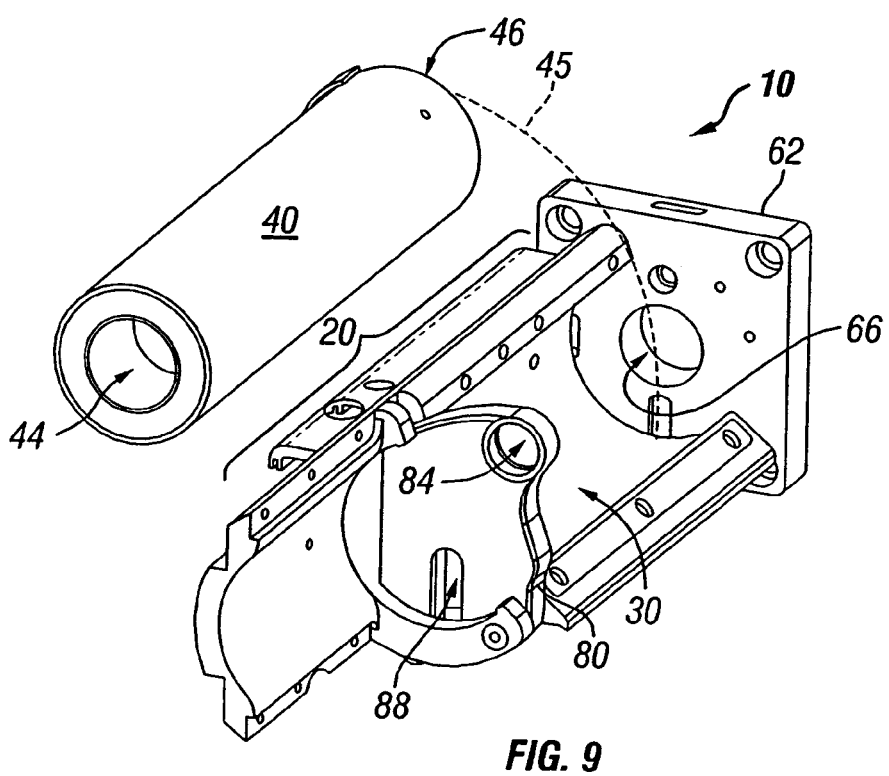
FIG. 9 is a second perspective view of the preferred embodiment of a pressure sleeve assembly in accordance with the present invention.

FIGS. 8–9 show an alternative embodiment of a pressure sleeve assembly 10 in accordance with the present invention wherein the door 80 of the assembly 10 is removable from the longitudinal base member 20. A removable door 80 can be included in a pressure sleeve assembly having a cylinder 40 that is coupled to the longitudinal base member 20 by a pivotal arm 50 as in FIGS. 2–7. Alternatively, as shown in FIG. 9, a removable door 80 can be included in a pressure sleeve assembly 10 having a cylinder 40 which is manually insertable and removable from the receptacle area 30.

In a preferred embodiment, the removable door 80 can include a hole 84 along an upper corner of the door 80 which serves as a "finger holster" 84 through which the user can insert a finger to grasp and remove the door. Additionally, the base of the removable door 80 can include a groove 26 which engages into corresponding structure located within a slot 22 in the longitudinal base member 20 so as to secure the removable door 80 when it is moved into place. The removable door 80 can also include an index pin 83 which also engages with a corresponding receptacle or structure 24 in the slot 22 of the longitudinal base member 20 to further secure the removable door 80 into place. The longitudinal base member 20 can also include a guide slot 26 located along an upper edge of bar number 20 in alignment with the slot 22 of the longitudinal base member 20. The guide track 26 guides the removable door 80 into place as the door 80 is moved down into place and serves as additional support for the removable door 80 when in place.

An advantage of a pressure sleeve assembly 10 having a removable door 80 is improved accessibility to component parts of the assembly 10, such as the cylinder 40 and syringe 25. A removable door 80 also improve maintenance and more reliable repeated use of the assembly by allowing for complete cleaning of the door 80 and the area of the longitudinal member 20 surrounding its site of insertion 22. This advantage reduces the possibility of contrast media or other fluid from accumulating and crystallizing and causing the door to be stuck into place. A removable door 80 also allows use of the pressure sleeve assembly with syringes having a variety of configurations. For example, the slot 88 of the removable door 80 can be located at different sites on the door so as to accommodate varying neck region configurations of different syringe types.

When a syringe 25 has been placed into the receptacle area 30, the endplate 62 covers the second opening 46 of the cylinder 40 and the removable door 80 covers the first opening 44 of the cylinder 40. To open the assembly 10, the removable door 80 is lifted upward and out of the slot 22 (FIG. 8). Removal and insertion of the cylinder 40 can be achieved by either placing the cylinder 40 directly into the receptacle area 30 or by sliding the cylinder 40 into the receptacle area 30 from the front area of the longitudinal base member 70. In this fashion, the removable door 80 serves as a "hardware lock" to the pressure sleeve assembly 10 by holding the cylinder 40 in place.

In this embodiment, the cylinder 40 may be retained in place by the frictional contact and engagement of certain surfaces in the receptacle area 30 contacting the outer surfaces of the pressure sleeve 40. In one embodiment, the certain surfaces could be the rail structures extending longitudinally along the receptacle area of the pressure sleeve assembly 10. In such an embodiment, the structure defining the receptacle area generally leaves an approximately 180 degree opening for receiving the sleeve 40.

In one particular embodiment, the structure forming the receptacle area 30 may include a electrical luminescent ("EL") strip or backlight foam structure layered on the surfaces defining the receptacle area 30. In such an embodiment, the rail structures in association with the EL layer form a complaint surface that snugly receives and retains the pressure sleeve 40.

As described above, a pressure sleeve assembly 10 can be used for a variety of medical treatments where injection of a fluid is desired in a medical procedure. Depending upon the particular medical procedure, the pressure sleeve assembly 10 can be used to deliver a variety of fluids. For example, in certain angiographic applications, the assembly can be used to deliver contrast media via a catheter to a patient suffering from a problematic cardiovascular or other vascular condition. In such a procedure, the contrast media will preferably have a viscosity between 2 and 30 centipoise (for all functions at the temperatures used). The contrast media can be injected by the syringe 25 contained within the cylinder 40 of the pressure sleeve assembly 10 through angiography catheters rated for a maximum 1200 psi pressure with flow rate of about 40 ml/sec.

The manner of loading the syringe 25 into the pressure sleeve assembly 10 varies somewhat according to several embodiments of the invention.

In the embodiment of a rotatable cylinder assembly 10, the cylinder is rotated into the open position. The syringe 25 is then loaded into the cylinder 40 (either front-loaded, or if suitable, rear-loaded) and the cylinder 40 rotated back into the closed position. Alternatively, if the pressure sleeve assembly 10 includes a removable door 80 with non-rotatable cylinder, the door 80 is slid out of position to expose the first opening 44 of the cylinder 40. The syringe is then front-loaded into the cylinder 40 and the door 80 replaced back into position covering the first opening 44 of the cylinder 40. As discussed above, various embodiments of the pressure sleeve assembly 10 offer particular advantages relating to the simplification of the loading and cleaning of the device.

The present invention also contemplates a method of assembly or fabricating a pressure sleeve assembly 10. Various materials can be used for constructing a pressure sleeve assembly 10, so long as the material used for the cylinder 40 is sufficiently rigid and durable so as to withstand the level of pressure or force exerted by the fluid contained within the cylinder 40. This level of pressure or force may vary depending upon the particular procedure being performed and the use or type of fluid being used. Preferably, materials used to fabricate the pressure sleeve assembly will be of a non-rusting or non-corrosive, rigid type of material such as stainless steel, aluminum or plastic. Additionally, the configuration and size of the pressure sleeve assembly 10, particularly of the cylinder 40, can be adapted to be compatible with a variety of injection systems as well as to hold a variety of syringe sizes and shapes.

Due to high-pressure forces created within the syringe 25 during fluid injection, substantial structural support is needed to contain the syringe 25 and its fluid contents. Therefore, the cylinder 40 which houses the syringe 25, is preferably manufactured from a material of suitable strength or thickness to withstand about 1 to 2000 psi, or preferably of about 200 to 1200 psi. It is also preferable that the cylinder 40 be made of a generally clear material so that the user can visually check the syringe 25 and its fluid contents during a procedure.

Method For Use of a Pressure Sleeve Assembly with a Fluid Injection System

The present invention also contemplates a method of using a pressure sleeve assembly 10 in a fluid injection system for delivery of fluid to patient. The method includes providing a pressure sleeve assembly as described above and shown in FIG. 1. Referring to FIG. 1, the system 100 includes a power supply (not shown), a control panel 210 and an injector head 220 having a pressure sleeve assembly 10. The power supply connects to the injector head 220, providing power to the fluid injection system and electrical safety separation of the fluid injection system 100 from a main power source. As disclosed in the pending applications discussed above (and incorporated by reference), the injector head 220 houses electrical controls and sensors for the fluid injection system 100. The injector head can be designed so as to be free standing or mountable on for example, a patient's bed rail, pedestal cart, or other supportive structure. The control panel 210 is connected to the injector head 220 and can be connected by cable or may be connected by wireless connection such as radio frequency, infrared optic, or ultrasonic link. The control panel 210 can include a display screen 212, visible and audible indicators, as well as control switches or buttons to provide operator controls and prompts. The control panel 210 functions as the user interface providing operation prompts, status information, and alerts prior to and during use of the fluid injection system.

The pressure sleeve assembly 10 is coupled to the injector head 220. The pressure sleeve assembly 10 can also include additional components to facilitate its use with a fluid injection system such as, for example, lighting 410 to facilitate manual bubble detection within a fluid line, a cradle 420 for holding or hanging a fluid source. The pressure sleeve assembly 10 can also include additional sensors or components for detecting the status of various components, such as the presence of air in the fluid line or the level of fluid or contrast media in the bottle.

Also included, if desired, for use with the fluid injection system are accessory items such as disposable angiographic kits. Included in such kits are single use items such as syringe, valves, tubing, high-pressure tube extension, stopcocks, patient manifold, cables, pressure transducer, and/or other components, which aid or provide interface between the system, the patient and the operator. Such items are available in the art and described, for example, in the publication entitled ACIST™ System Operator's Guide (supra).

In a preferred embodiment, a pressure sleeve assembly 10 is intended for use with an angiographic system that supplies radio-opaque contrast media to a catheter at a user-determined variable flow rate which can be instantaneously and continuously varied. Such a system is described, for example in ACIST™ System Operator's Guide (Copyright 1999 for ACIST™ Model CL100H Injection System; ACIST Medical Systems, Inc., 7450 Flying Cloud Drive, Suite 150, Eden Prairie, Minn. 55344). Alternatively, a pressure sleeve assembly as disclosed herein, can also be used with a variety of Angiographic or other Fluid Injector Systems described in co-pending U.S. application Ser. No. 08/488,443 filed Jan. 20, 2000, U.S. application Ser. No. 08/966,088 filed Nov. 7, 1997, U.S. application Ser. No. 08/957,228 filed Oct. 24, 1997 and U.S. application Ser. No. 08/957,801 filed Oct. 24, 1997, as well as U.S. Pat. Nos. 5,800,397, 5,988,587 and 5,573,515, the disclosures of which are hereby incorporated by reference in their entirety The present invention provides efficient and reliable delivery of fluid in a medical procedure. The features of the invention, as described herein, provide a fluid injection assembly and system that is less cumbersome to use, easier to maintain and more versatile for the user.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

All publications and patent applications in this specification are herein incorporated by reference to the same extent as if each individual publication or patent application was specifically and individually indicated by reference.

What is claimed is:

1. A device for injecting medical fluid comprising:
   a. an injector head;
   b. a syringe sized to be placed into said injector head;
   c. a cylinder having an opening sized to receive at least a portion of said syringe;
   d. a receptacle on said injector head sized to receive said cylinder;
   e. said cylinder being connected to said injector head and being selectively rotatable on said injector head into and out of said receptacle.

2. A device as in claim 1, further comprising a longitudinal base member located at one end of said injector head, said longitudinal base member containing said receptacle and said cylinder being attached to said longitudinal base member.

3. A device as in claim 2, further comprising a forward plate mounted on said longitudinal member at a position forward of said receptacle.

4. A device as in claim 3, wherein said forward plate includes a slot for receiving a portion of said syringe.

5. A device as in claim 4, wherein said slot receives an exit port of said syringe.

6. A device as in claim 5, wherein said slot generally forms an arc with a radius equivalent to the arc circumscribed by said exit port as said cylinder is rotated into and out of said receptacle.

7. A device as in claim 1, wherein said cylinder includes a slot for receiving a portion of said syringe.

8. A device as in claim 7, wherein said slot receives an inlet port of said syringe.

9. A device as in claim 3, wherein said forward plate includes a sensor that senses an operating parameter of said device.

10. A device as in claim 9, wherein said operating parameter indicates the presence of said syringe in said cylinder.

11. A device as in claim 9, wherein said operating parameter indicates the force exerted by said syringe on said forward plate.

12. A device as in claim 1, further comprising a grasping portion projecting from said cylinder.

13. A device as in claim 2, further comprising an attachment plate for connecting said longitudinal base member to said injector head, said attachment plate positioned at a location rearward of said receptacle.

14. A device as in claim 13, wherein said attachment plate includes a protrusion which engages a corresponding receptacle in said cylinder.

15. A device as in claim 13, wherein said attachment plate includes a sensor serving configured to indicate when said cylinder is fully engaged in said receptacle.

* * * * *